United States Patent [19]

Jones

[11] Patent Number: 4,555,504

[45] Date of Patent: Nov. 26, 1985

[54] INCLUSION COMPLEX OF β-CYCLODEXTRIN AND DIGOXIN

[75] Inventor: Harry P. Jones, Erith, England

[73] Assignee: Burroughs Wellcome Co., Research Triangle Park, N.C.

[21] Appl. No.: 589,035

[22] Filed: Mar. 12, 1984

Related U.S. Application Data

[63] Continuation of Ser. No. 341,236, Jan. 21, 1982, abandoned.

[30] Foreign Application Priority Data

Jan. 23, 1981 [GB] United Kingdom ............... 8102124

[51] Int. Cl.$^4$ .............................................. A61K 31/70
[52] U.S. Cl. ........................................ 514/26; 536/5; 536/6; 536/103
[58] Field of Search ............... 536/5, 6, 103; 424/182, 424/361; 514/26

[56] References Cited

U.S. PATENT DOCUMENTS 3,541,077 11/1970 Armbruster ..................... 536/103
4,083,969 4/1978 Inoue et al. ..................... 424/182

Primary Examiner—Johnnie R. Brown
Assistant Examiner—Elli Peselev
Attorney, Agent, or Firm—Donald Brown

[57] ABSTRACT

Inclusion complexes of cyclodextrins, particularly β-cyclodextrin, and cardiac glycosides, particularly digoxin, are disclosed. The complexes have high aqueous solubility and are useful in the preparation of pharmaceutical formulations containing cardiac glycosides for use in therapy.

7 Claims, No Drawings

INCLUSION COMPLEX OF β-CYCLODEXTRIN AND DIGOXIN

This application is a continuation of application Ser. No. 341,236, filed 1,21,82 now abandoned.

The present invention relates to complexes to saccharide-containing compounds with cycloamyloses, their preparation and their use. In particular the invention is concerned with complexes of pharmacological interest.

Inclusion complexes of compounds with cycloamyloses, in particular cyclodextrins, are well known. Cyclodextrins are cyclic molecules consisting of 6,7, or 8 glucopyranose units linked as B-1,4-glucoside units. Structurally they are characterised by a special arrangement of hydroxyl groups whereby the outer surface of the ring formed by the cyclodextrin is hydrophilic, ensuring water solubility, whilst the inner surface is lipophilic permitting molecules (known as guest molecules) or parts thereof which are less polar than water and are of suitable dimensions to penetrate the lipophilic cavity in aqueous solution.

A difficulty well recognised in the field of pharmaceuticals is that associated with poor aqueous solubility which may make formulations more difficult to prepare or cause other problems such as dissolution difficulties and hence poor or variable bioavailability. This is particularly so with compounds which have a very low aqueous solubility. Complexing with cyclodextrins has been employed to overcome these problems but it is not invariably effective.

One class of pharmaceuticals which have poor solubility in water are the cardiac glycosides of which the most notable is digoxin. It is generally recognised that drugs having a solubility in water at 37° C. of less than 1% w/v are particularly prone to bioavailability problems. The solubility of digoxin is in the order of 0.005% in water and the question of bioavailability of compounds such as cardiac glycosides is particularly pertinent as they have a very low therapeutic index.

It has now been found, contrary to expectation, that complexes of the cardiac glycosides with cyclodextrins can be formed, that such complexes enhance the aqueous solubility of the cardiac glycosides and that the increase in solubility is much greater degree than could have been expected. The surprisingly high increase in solubility is sufficient to ameliorate the problems associated with poor solubility and in favourable circumstances increases the solubility to more than 1% w/v. We have also found that the complex does not adversely affect the absorption of the drug on administration.

Although inclusion complexes of compounds with cyclodextrins in which the guest molecule is a compound having useful pharmacological properties have been described, no complexes in which the guest molecule has the type of structure associated with cardiac glycosides are known. Further although inclusion complexes have been described as increasing the aqueous solubility of poorly soluble compounds the degree of increase observed (a maximum of from about 5 to 10 folds) is much lower than that found for cardiac glycosides and would be insufficient to overcome the problems associated with the poor solubility of the cardiac glycosides.

The present invention accordingly provides an inclusion complex of a cardiac glycoside with a cyclodextrin.

The α-cyclodextrin may comprise one or more of α-cyclodextrin, β-cyclodextrin and γ-cyclodextrin. Preferably the α-cyclodextrin is β-cyclodextrin.

By cardiac glycoside is meant a compound bearing one or more glycoside residues and which exhibit a pharmacological effect on heart function. Such cardiac glycosides include for example those compounds identified as such in Martindale, The Extra Pharmacopoiea (26th Edition) page 617 et seq.

Specific cardiac glycosides suitable for complexing with cyclodextrins include digitoxin, gitoxin, diginin, deslanoside, lanatosides A, B and C, and, preferably, digoxin. Conveniently the cardiac glycoside oligosaccharide side chain comprises at least three monosaccharide residues.

The complexes of the invention may be prepared by any method known in the art for the preparation of complexes of cyclodextrins.

Such methods involve, in general, the mixing of a solution of the cardiac glycoside with an aqueous solution of the cyclodextrin and isolating the so formed product.

The cardiac glycoside may be dissolved in water or an organic solvent (either miscible or immiscible with water). Convenient solvents include for example diethylether, tetrahydrofuran, dioxan, acetone, dimethylsulphoxide, dimethylformamide and lower aliphatic alcohols. Preferably the cardiac glycoside is dissolved in either water or a mixture of water and a water-miscible solvent such as methanol or ethanol.

The complex may be isolated by any suitable technique for example lyophilisation or evaporation of the solvent, precipitation or low temperature crystallisation.

The ratio of cyclodextrin to compound used to prepare the complexes of the invention may be any convenient ratio but conveniently the cyclodextrin is in a molar excess. The benefits derived from the invention may be obtained by having the molar ratio of cyclodextrin to compound in the range of 10:1 to 1:10 preferably 2:1 to 5:1 for example 3:1 and by using the methods and ratios described above complexes are conveniently obtained containing up to 20% w/w of the cardiac glycoside. However in view of the low doses of the cardiac glycoside normally administered and the difficulty of preparing homogenous mixtures of active ingredient and excipients it may be desirable to prepare the complex with an excess of the cyclodextrin present, for example complex containing in the order of 0.10 l to 1% by weight of the cardiac glycoside, particulary in the range 0.05 to 0.2% by weight.

The complexes of the invention comprise a more convenient way of administering the cardiac glycosides (which have utility in the treatment of cardiac disfunction), the cyclodextrin acting merely as a solubilizing agent and not altering the therapeutic behaviour of the drug in any way. Thus the complexed cardiac glycosides may be administered in those dosage ranges in which they are administered in non-complexed form. For example digoxin is normally administered to adults in doses of about 0.25 to 1.5 mg.

The invention also provides an inclusion complex as defined herein for use in human or veterinary medicine.

The complex, for use as a pharmaceutical, may be presented as the raw chemical but is preferably presented as a pharmaceutical formulation.

The invention therefore provides in a further aspect a pharmaceutical formulation comprising an inclusion complex of a cardiac glycoside with a cyclodextrin together with a pharmaceutically acceptable carrier therefor and optionally other therapeutic and/or prophylactic ingredients. The carriers must be 'acceptable' in the sense of being compatible with the other ingredients of the formula and not deleterious to the recipient thereof. Suitably the pharmaceutical formulation will be in unit dosage form. Each unit dose will conveniently contain that amount of cardiac glycoside normally incorporated into a unit dose of such drug in the absence of a cyclodextrin. For digoxin each unit dose will conveniently contain from 0.01 to 1 mg of active ingredient.

The pharmaceutical formulations may be any formulation in which the inclusion complexes may be administered and include those suitable for oral or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers of both and then, if necessary, shaping the product into the desired formulation.

Pharmaceutical formulations suitable for oral administration wherein the carrier is a solid are most preferably presented as unit dose formulations such as boluses, capsules, cachets or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Moulded tablets may be made by moulding an inert liquid diluent. Tablets may be optionally coated and, if uncoated, may optionally be scored. Capsules may be prepared by filling the active compound, either alone or in admixture with one or more accessory ingredients, into the capsule cases and then sealing them in the usual manner. Cachets are analogous to capsules wherein the active ingredient together with any accessory ingredient(s) is sealed in a rice paper envelope.

Pharmaceutical formulations suitable for oral administration wherein wherein the carrier is a liquid may conveniently be presented as a solution in an aqueous liquid or a non-aqueous liquid, or as an oil-in-water or water-in-oil liquid emulsion. Pharmaceutical formulations suitable for parenteral administration are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The invention is illustrated in the following examples which are not intended to be a limitation thereof.

EXAMPLE 1

Preparations of an inclusion complex of digoxin and B-cyclodextrin (a) Digoxin (0.78 g; 0.001 mole) and B-cyclodextrin (3.42 g; 0.003 mole) were mixed in a beaker with deionised water (10 ml), ultrasonicated and then diluted with water to give a final volume of 200 ml. After stirring complete solution was obtained; the so obtained solution was transferred to a rotary evaporator and the water removed under reduced pressure whilst heating at 70° C. The flask and residue were dried in a vacuum oven at 70° C., the residue removed from the vessel, transferred to a pestle and mortar, ground to a fine powder and dried to constant weight at 70° C. under reduced pressure.

(b) B-cyclodextrin (3.42 g; 0.003 mole) was dissolved in deionised water (200 ml). To this solution was added digoxin (0.78 g; 0.001 mole) and the mixture stirred at ambient temperature until the digoxin dissolved. The obtained solution was transferred to stoppered vials and the solvent removed by lyophilisation at $-40°$ C., providing a complex of B-cyclodextrin and digoxin.

EXAMPLE 2

Preparation of a complex of digitoxin and B-cyclodextrin

A complex of digitoxin and B-cyclodextrin was prepared by the method of Example 1(a) with exception that the amounts of digitoxin and B-cyclodextrin used were respectively $10^{-4}$ mole and $10^{-2}$ mole.

EXAMPLE 3

Comparative solubility of complexed and non-complexed cardiac glycosides

Either complexed (as described in Examples 1 and 2) or non-complexed material (approximately 500 mg) was added to deionised water (5 ml) in a test-tube and the mixture shaken for about 8 hours at ambient temperature. The resultant mixture was filtered through a filter paper (Whatman No. 2) and then through a membrane filter (0.02 um, Millipore), the filtrate diluted 100 fold with deionised water and the solution thus obtained assayed for cardiac glycoside in a conventional manner using high performance liquid chromatography.

The results are given below:

| Cardiac Glycoside | Solubility | |
|---|---|---|
| | Non-complexed | Complexed |
| Digoxin | 46 mg/liter (0.0046%) | 16,700 mg/liter (1.67%) |
| Digitoxin | 8.2 mg/liter (0.0008%) | 253 mg/liter (0.0253%) |

EXAMPLE 4

Comparative dissolution of complexed and non-complexed digoxin

The dissolution rate of complexed (1:3 complex, Example 1) and non-complexed digoxin was determined in the British Pharmacopoeia rotating basket apparatus (B.P., 1980). The dissolution medium was deionised water (1 liter) at 37° C. A scoop containing sample (about 12.5 g of digoxin or about 50 g of digoxin/B- cyclodextrin complex) was added to the dissolution medium and allowed to settle to the base of the vessel. Samples (2 ml) were taken at intervals up to 60 minutes via a volumetric pippette and assayed by high performance liquid chromatography to determine cumulative percentage release of drug. The results are shown below:

| Sample | $T_{80}$ (time for 80% release) |
| --- | --- |
| Digoxin | >60 minutes |
| Digoxin/B-cyclodextrin Complex | <5 minutes |

EXAMPLE 5

Simulated absorption rate of complexes of the invention

The simulated absorption rate of complexed cardiac glycosides of the invention and the corresponding non-complexed cardiac glycosides was determined in conventional manner on a Sartorius absorption simulator as described by Jones and Bye, J. Pharm. Pharmacol. 1979, 31, 730–733. The simulated absorption rate is a model of absorption through the gut wall.

Phase I was prepared by dissolving the complex or compound (50 mg) in deionised water (100 ml). Phase II was prepared by dissolving B-cyclodextrin in deionised water (100 ml). The intestinal lipid mixture was employed with a 40 cm² diffusion cell. Aliquots (2 ml) were removed from both chambers at 0, 60, 120, 180, and 240 minutes. The cardiac glycoside content of the solution was determined by standard methods employing HPLC. The absorption rate (KI) was calculated in a conventional manner. The results are shown below:

| Sample | KI |
| --- | --- |
| Digoxin | 0.019–0.025 min$^{-1}$ |
| Complex of Example 1 | 0.027 to 0.029 min$^{-1}$ |

EXAMPLE 6

Pharmaceutical Formulations (a) Digoxin Tablet containing 0.25 mg Digoxin

| | |
| --- | --- |
| Digoxin/B-cyclodextrin complex (1:3) | 1 mg |
| Lactose | 87 mg |
| Maize Starch | 10 mg |
| Hydrolysed Starch | 2 mg |
| Magnesium Stearate | 1 mg |
| Total | 100 mg |

(b) Digoxin Tablet containing 0.125 mg digoxin

| | |
| --- | --- |
| Digoxin/B-cyclodextrin complex (1:100) | 12.625 mg |
| Lactose | 75 mg |
| Maize Starch | 10 mg |
| Gelatin | 2 mg |
| Magnesium Stearate | 1 mg |
| Total | 100.625 mg |

(c) Digoxin injection containing 0.5 mg digoxin

| | |
| --- | --- |
| Digoxin/B-cyclodextrin complex (1:3) | 2 mg |
| Water for injection to | 2 ml. |

(d) Digoxin capsule containing 0.125 mg digoxin

| | |
| --- | --- |
| Digoxin B-cyclodextrin complex (1:3) | 0.5 mg |
| Lactose | 75 mg |
| Maize Starch | 10 mg |
| Magnesium Stearate | 1 mg |
| filled into a soft gelatin capsule | |

(e) P Solution containing per ml. digoxin

| | |
| --- | --- |
| Digoxin B-cyclodextrin complex (1:3) | 0.2 g |
| Methylhydroxybenzoate | 1 g |
| Sucrose | 300 g |
| Colouring | 0.25 g |
| Flavour | 1 ml |
| Purified water q.s. | 1000 ml |

I claim:

1. A pharmaceutical composition comprising a nontoxic, effective cardiac dysfunction treatment amount of an inclusion complex of β-cyclodextrin and digoxin together with a pharmaceutically acceptable carrier therefor.

2. A method for the treatment of cardiac dysfunction in a mammal in need thereof which comprises administration to said mammal of a nontoxic, effective cardiac dysfunction treatment amount of an inclusion complex of β-cyclodextrin and digoxin.

3. The method of claim 2 wherein the mammal is a human being.

4. Inclusion complexes of β-cyclodextrin and digoxin.

5. A complex according to claim 4 wherein the molar ratio of β-cyclodextrin to digoxin is in the range from 10:1 to 1:10.

6. A complex according to claim 4 wherein the molar ratio of β-cyclodextrin to digoxin is in the range from 2:1 to 5:1.

7. A complex according to claim 4 wherein the digoxin is present in an amount of from 0.01% to 1% by weight.

* * * * *